(12) United States Patent
Menon et al.

(10) Patent No.: US 7,620,439 B2
(45) Date of Patent: Nov. 17, 2009

(54) CONDUCTIVE ADHESIVES AND BIOMEDICAL ARTICLES INCLUDING SAME

(75) Inventors: Vinod P. Menon, Woodbury, MN (US); Kanta Kumar, Maplewood, MN (US); Carl T. Nelson, Oakdale, MN (US); Don A. Rizzardi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 493 days.

(21) Appl. No.: 11/197,216

(22) Filed: Aug. 4, 2005

(65) Prior Publication Data

US 2007/0032719 A1 Feb. 8, 2007

(51) Int. Cl.
*A61B 5/04* (2006.01)
*H01B 1/12* (2006.01)
*H01B 1/00* (2006.01)

(52) U.S. Cl. ............... 600/391; 600/392; 252/500
(58) Field of Classification Search .......... 600/391–392
See application file for complete search history.

(56) References Cited

U.S. PATENT DOCUMENTS

| | | | |
|---|---|---|---|
| 3,679,534 A * | 7/1972 | Weinberg ............... 428/118 |
| 4,352,359 A | 10/1982 | Larimore et al. |
| 4,524,087 A | 6/1985 | Engel |
| 4,539,996 A | 9/1985 | Engel |
| 4,554,924 A | 11/1985 | Engel |
| 4,588,762 A * | 5/1986 | Mruk et al. ............... 524/45 |
| 4,715,382 A | 12/1987 | Strand |
| 4,771,713 A | 9/1988 | Kinzenbaw |
| 4,771,783 A | 9/1988 | Roberts |
| 4,830,776 A | 5/1989 | Thompson |
| 4,846,185 A | 7/1989 | Carim |
| 4,848,348 A | 7/1989 | Craighead |
| 4,848,353 A | 7/1989 | Engel |
| 5,012,810 A | 5/1991 | Strand et al. |
| 5,133,356 A | 7/1992 | Bryan et al. |
| 5,215,087 A | 6/1993 | Anderson et al. |
| 5,230,701 A | 7/1993 | Meyer et al. |
| 5,276,079 A | 1/1994 | Duan et al. |
| 5,338,490 A * | 8/1994 | Dietz et al. ............... 252/500 |
| 5,505,200 A | 4/1996 | Takaki |
| 5,506,059 A | 4/1996 | Robbins et al. |

(Continued)

FOREIGN PATENT DOCUMENTS

JP    SHO 62-321    1/1987

(Continued)

*Primary Examiner*—Lee S Cohen
(74) *Attorney, Agent, or Firm*—Nicole J. Einerson

(57) ABSTRACT

A conductive adhesive composition is provided and articles that include the adhesive composition as a component thereof. The conductive adhesive composition comprises: (a) pressure sensitive adhesive; (b) electrolyte comprising water soluble or water dispersible organic chloride; and (c) humectant. In some embodiments, the conductive adhesive composition is a bicontinuous composition comprising an aqueous phase and an oil phase, and the bicontinuous composition may be derived from a polymerizable microemulsion composition, the microemulsion composition comprising: an aqueous phase comprising one or more hydrophilic monomers or oligomers and/or one or more amphiphilic monomers or oligomers in water, the water-soluble or water-dispersible organic chloride, surfactant and humectant; and an oil phase comprising one or more hydrophobic monomers or oligomers. Biomedical articles such as biomedical electrodes, may incorporate the foregoing adhesive as a component.

59 Claims, 2 Drawing Sheets

U.S. PATENT DOCUMENTS

| | | |
|---|---|---|
| 5,670,557 A | 9/1997 | Dietz et al. |
| 5,674,561 A | 10/1997 | Dietz et al. |
| 5,686,516 A * | 11/1997 | Tzur ......................... 524/394 |
| 6,232,366 B1 * | 5/2001 | Wang et al. ................. 523/111 |
| 6,623,664 B2 * | 9/2003 | Takaki et al. ................ 252/511 |
| 6,709,716 B2 | 3/2004 | Uy et al. |
| 6,792,301 B2 * | 9/2004 | Munro et al. ............... 600/391 |
| 6,842,636 B2 * | 1/2005 | Perrault et al. ............. 600/391 |

FOREIGN PATENT DOCUMENTS

| | | |
|---|---|---|
| WO | WO 01/48111 | 7/2001 |

* cited by examiner

CONDUCTIVE ADHESIVES AND BIOMEDICAL ARTICLES INCLUDING SAME

The present invention relates to conductive adhesive compositions and to biomedical articles that incorporate the conductive adhesive compositions as a component thereof.

BACKGROUND

Therapeutic and diagnostic medical procedures utilize equipment capable of processing electrical signals or electrical currents that are received from the body of a patient or are delivered to the patient's body. In these procedures, the interface between the patient's skin and the applicable equipment typically includes a biomedical electrode constructed to include a conductor connected electrically to the medical equipment and a conductive medium that is adapted for contact with the patient's skin (e.g., with an adhesive).

By way of example, biomedical electrodes are employed in therapeutic procedures and equipment such as in transcutaneous electronic nerve stimulation (TENS) devices that are used for pain management; neuromuscular stimulation (NMS) techniques for the treatment of certain conditions such as scoliosis; defibrillation electrodes for dispensing electrical energy to a patient's chest cavity to defibrillate the heart; and dispersive electrodes that receive electrical energy that has been applied to an incision made during electrosurgery. Biomedical electrodes are also employed in diagnostic procedures and equipment that include electrocardiography for monitoring heart activity and diagnosing heart abnormalities.

Non-polarizable electrodes, and in particular electrodes made with silver and/or silver chloride are highly stable and have been widely used in diagnostic applications. In low-cost versions, these electrodes are often coated in thin sections of conductive ink on an insulating backing. Conductive inks formulated for these applications typically include silver/silver chloride particles and a polymeric binder. A conducting adhesive (e.g., a hydrogel or hydrocolloid) is laminated to the silver-coated backing, and the assembly is die cut to the required electrode shape. The conductive adhesive serves the dual purpose of providing adhesion of the electrode to the skin as well as permitting electrical transduction of the electrical activity of the heart. The adhesive layer of the electrodes are protected with a release liner prior to the application of the electrode to the skin.

The monolithic adhesive construction of typical non-polarizable electrodes has been problematic because of an exposed edge of adhesive along the perimeter of the electrode. The ionically conductive phase of the adhesive consists of an alkali or alkaline earth metal chloride (typically potassium or sodium chloride) dissolved in water with an optional humectant added to slow down evaporative loss. However, under low humidity conditions (which can be as low as 20% R.H in hospitals), rapid evaporative loss of water occurs along with an accompanying degradation of the electrical properties of the electrode. The electrical properties are related to the conductance of dissolved salt in the water/humectant mixture of the adhesive. As water evaporates, the humectant concentration increases. Because alkali and alkaline earth halides are poorly soluble in commonly used humectants, the ionic concentration of the adhesive is compromised and the electrical properties degrade.

There is a need for improved conductive adhesives and for articles comprising such adhesives including biomedical articles such as biomedical electrodes, for example.

SUMMARY

The present invention provides conductive adhesives and articles comprising such adhesives. In one aspect, the invention provides a conductive adhesive composition, comprising:

(a) pressure sensitive adhesive;

(b) electrolyte comprising water soluble or water dispersible organic chloride; and (c) humectant.

In another aspect, the invention provides a biomedical electrode, comprising:

a conductor member; and a conductive adhesive composition associated with the conductor member, the conductive adhesive composition, comprising:

(a) pressure sensitive adhesive;

(b) electrolyte comprising water soluble or water dispersible organic chloride; and (c) humectant.

As used herein, "onium" cations refers to polyatomic cations formed by adding more protons to monatomic anions than are required to give a neutral unit. Such cations are referred to with the ending-onium. Substituted derivatives may be formed from the basic cations, e.g. hydroxylammonium, tetramethylstibonium, dimethyl oxonium $(CH_3)_2OH^+$. Inorganic onium cations include "ammonium", "phosphonium", "oxonium", "sulfonium", "chloronium", "bromonium" and "iodonium."

The terms "organic phase," "oil phase," "oleophilic," "hydrophobic" and "lipophilic phase" are used interchangeably herein.

Those skilled in the art will further understand the features of the present invention upon consideration of the remainder of the disclosure herein, including the Detailed Description together with the various Figures as well as the appended claims.

BRIEF DESCRIPTION OF THE DRAWINGS

In describing aspects of the disclosed embodiments, reference is made to the drawings wherein structural features are identified with reference numbers and wherein like numbers indicate like features.

DETAILED DESCRIPTION

Figure 1:
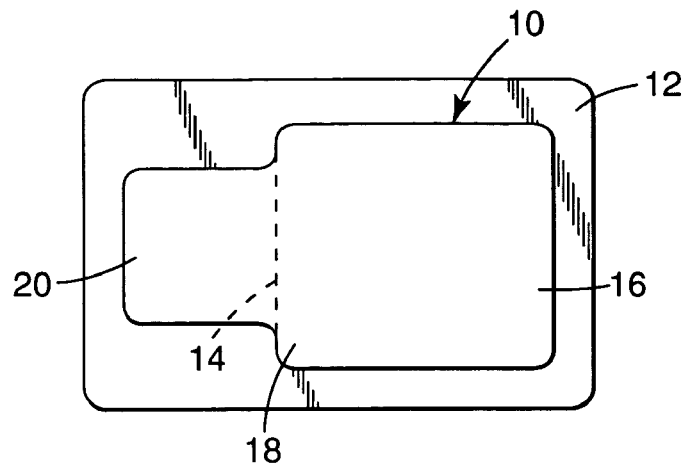
FIG. 1 is a top plan view of an embodiment of a biomedical electrode useful for the diagnosis or monitoring of heart conditions in a mammalian patient, the electrode including a conductive adhesive according to the present invention.

The present invention provides conductive adhesives that can be used as electrically conductive components in an article such as a biomedical article including a biomedical electrode, for example. The conductive adhesives of the invention are resistant to the loss of electrical properties following a loss of moisture (e.g., water) from the adhesive. In embodiments of the invention, the conductive adhesive is a pressure sensitive adhesive (PSA) comprising an organic chloride electrolyte and compatible humectant. In some embodiments, the conductive adhesive is a bicontinuous, conductive, PSA having an aqueous phase and an oil phase with an organic chloride electrolyte compatible humectant and surfactant in the aqueous phase. In some embodiments, the conductive adhesive is in the form of a hydrogel. In other embodiments, the PSA is a component in an article such as a biomedical electrode, for example.

The adhesive of the invention can be prepared in any of a variety of processes. In some embodiments, the adhesive is prepared by way of a microemulsion that is of a viscosity suitable for coating onto a backing. The polymerized microemulsion PSA according to the present invention can be derived from polymerization of a free-radically polymerizable hydrophilic and/or amphiphilic monomers or oligomers in an aqueous phase with concurrent polymerization of free-radically polymerizable hydrophobic and/or amphiphilic monomers or oligomers in an organic (oil) phase. The resulting PSA can have a bicontinuous structure which, in some embodiments, may comprise two solid, substantially nonporous bicontinuous phases.

Bicontinuous Adhesive Compositions

In embodiments of the invention, bicontinuous adhesive compositions are provided by the polymerization of suitable monomers and/or oligomers provided in the form of polymerizable microemulsion compositions. Prior to polymerization, the microemulsions typically include an aqueous phase that comprises water, free radically (co)polymerizable ethylenically unsaturated polar hydrophilic or amphiphilic monomer(s) or oligomer(s), initiator, organic chloride electrolyte, humectant, surfactant and optional additives. The organic or oil phase typically comprises (co)polymerizable ethylenically unsaturated hydrophobic or amphiphilic monomer(s) or oligomer(s). Components of the microemulsion may be added in any logical order. For example, components may be initially combined in two or more separate blends. The initial blends may subsequently be combined to form a microemulsion. Components of a suitable microemulsion are discussed below.

Water

Microemulsion compositions generally comprises from about 2 to about 50 percent by weight of water (e.g., deionized water). In some embodiments, the compositions comprise from about 5 to about 30 percent by weight and, in some embodiments, from about 6 to about 25 percent by weight, based upon the total weight of the microemulsion. The water phase may include water-soluble and/or water-dispersible additives selected to provide certain properties within the final PSA. To determine the most appropriate weight percent of water to be included in the microemulsion, the water can be added incrementally until a clear microemulsion region is achieved.

Ethylenically-Unsaturated Free-Radically (Co)Polymerizable Polar Species

At least one free-radically polymerizable ethylenically-unsaturated polar monomer or oligomer is included in the microemulsion. Suitable polar monomers or oligomers can be oil insoluble (hydrophilic) or can be partially water soluble and partially oil soluble (amphiphilic) so that they will dissolve in or become associated with an aqueous phase in the microemulsion. In some embodiments, the use of polar oligomers in the aqueous phase promotes formation of a substantially nonporous bicontinuous structure for the polymerized microemulsion PSA.

Monomers may generally be selected from the group consisting of polar monomers that are substantially insoluble in the oil phase and polar monomers other than oil-insoluble monomers (e.g., polar monomers which are both water soluble and oil soluble).

Microemulsions typically will comprise from about 2 to about 90 percent by weight of hydrophilic or amphiphilic monomers or oligomers. In some embodiments, the microemulsion will comprise from about 5 to about 70 percent by weight and, in other embodiments, from about 10 to about 60 weight percent, based upon the total weight of the microemulsion, depending upon the desired properties of the polymerized PSA.

Ethylenically-Unsaturated Free-Radically (Co)Polymerizable Polar Oligomers

Useful polar ethylenically-unsaturated free-radically (co)polymerizable oligomers which are substantially insoluble in the oil phase or which are both water soluble and oil soluble include but are not limited to polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures of two or more of the foregoing. In some embodiments, polyethylene oxide acrylates and diacrylates are used. Oligomers can have a number average molecular weight of about 100 to about 100,000. In some embodiments the number average molecular weight can range from about 100 to about 60,000, or from about 100 to about 5000. Molecular weight ranges may be selected to provide a PSA with optimal physical properties (e.g., water absorption, porosity, strength).

Ethylenically-Unsaturated Free-Radically (Co)Polymerizable Substantially Oil-Insoluble Polar Monomers An optional polar monomer for inclusion in the aqueous phase of a microemulsion is a water-soluble free-radically (co)polymerizable ethylenically-unsaturated polar monomer that is substantially insoluble in the oil phase. As used herein, "substantially oil-insoluble" and "water-soluble" mean that the monomer has a solubility of less than about 0.5% by weight in the oil phase and exhibits a distribution ratio at a given temperature (preferably about 25° C. to about 35° C.) of concentration in the oil phase to concentration in the aqueous phase of less than about 0.005. Such monomer may be nonionic such as acrylamide, for example, or such a monomer may be ionic. Mixtures of nonionic and ionic monomers may also be used.

Ionic monomers conforming to the foregoing criteria include but are not limited to sodium styrene sulfonate, potassium acrylate, sodium acrylate, sodium methacrylate, ammonium acrylate, sodium 2-acrylamido-2-methylpropanesulfonate, 4,4,9-trimethyl-4-azonia-7-oxa-dec-9-ene-1-sulfonate, N,N-dimethyl-N-(beta-methacryloxyethyl) ammonium propionate betaine, trimethylamine methacrylamide, 1,1-dimethyl-1-(2,3-dihydroxypropyl) amine methacrylamide, and other zwitterionic ethylenically-unsaturated monomers having the requisite solubility requirements, mixtures thereof, and the like. In some embodiments, oil-insoluble polar monomers include those selected from the group consisting of acrylamide, sodium styrenesulfonate, sodium acrylate, sodium 2-acrylamido-2-methylpropanesulfonate, sodium methacrylate, and mixtures thereof, due to ease of formulation and desirable properties when polymerized.

In some embodiments, it may be desirable to limit the amounts of anionic monomers in order to prevent the possible in situ formation of alkali metal or alkaline earth metal chlorides, the presence of which could result in a loss of conductivity if moisture is lost from the adhesive.

Other Ethylenically-Unsaturated Free-Radically (Co)Polymerizable Polar Monomers

Polar monomers can exhibit some solubility in both water and oil, having a solubility of about 0.5% or greater in the oil phase and exhibiting a distribution ratio at a given temperature (preferably about 25° C. to about 35° C.) of concentration in the oil phase to a concentration in the aqueous phase of greater than or equal to about 0.005. Useful polar ethylenically-unsaturated free-radically (co)polymerizable monomers partitionable between the aqueous phase and the oil phase of the microemulsion include but are not limited to N-vinylpyrrolidone, N-vinylcaprolactam, (meth)acrylic acid, hydroxyethyl (meth)acrylate, itaconic acid, styrene sulfonic acid, N-substituted acrylamides, N,N-disubstituted acrylamides, N,N-dimethylaminoethyl methacrylate, 2-acrylamido-2-methyl propane sulfonic acid, and mixtures thereof. In some embodiments, polar partitionable monomers include (meth)acrylic acid, N-vinylpyrrolidone, N-vinylcaprolactam, N,N-dimethylaminoethyl methacrylate, N,N-dimethylacrylamide, styrenesulfonic acid, 2-acrylamido-2-methylpropanesulfonic acid, and mixtures thereof.

In some embodiments, polar partitionable monomers can impart desired properties to the biphasic polymer composite, such monomers including acrylic acid, N-vinylpyrrolidone, N-vinylcaprolactam, N,N-dimethylacrylamide, and mixtures thereof.

Water-Soluble Initiators

The microemulsion may optionally comprise a water-soluble free-radical polymerization initiator. In some embodiments, the initiator is selected from the group consisting of thermal initiators, photoinitiators, and mixtures of the foregoing. Water soluble initiators dissolve in the aqueous phase of the microemulsion.

Water-Soluble Photoinitiators

Water-soluble photoinitiators useful in the present invention include photoinitiators that generate free radicals on exposure to electromagnetic (usually ultraviolet) radiation which initiates the (co)polymerization of the hydrophilic monomer(s), the oleophilic monomer(s), the (co)polymerizable oligomers, and (co)polymerizable surfactant as detailed below. Useful water-soluble photoinitiators include but are not limited to benzophenones substituted with an ionic moiety, a hydrophilic moiety or both; thioxanthones substituted with an ionic moiety, a hydrophilic moiety or both, and 4-substituted-(2-hydroxy-2-propyl)phenyl ketones, wherein the 4-substituent is an ionic or hydrophilic moiety. Ionic or hydrophilic moieties include but are not limited to hydroxyl groups, carboxyl groups, and carboxylic acid salt groups. Useful water-soluble benzophenones include but are not limited to 4-trimethylaminomethyl benzophenone hydrochloride and benzophenone sodium 4-methanesulfonate. Useful water-soluble thioxanthones include but are not limited to 3-(2-hydroxy-3-trimethylaminopropoxy) thioxanthone hydrochloride, 3-(3-trimethylaminopropoxy)thioxanthone hydrochloride, thioxanthone 3-(2-ethoxysulfonic acid)sodium salt, and thioxanthone 3-(3-propoxysulfonic acid) sodium salt. Useful water-soluble phenyl ketones include but are not limited to (2-hydroxy-2-propyl)(4-diethylene glycol phenyl) ketone, (2-hydroxy-2-propyl)(phenyl-4-butanecarboxylate) ketone, 4-(2-hydroxethoxy)phenyl-(2-propyl) ketone, and their water-soluble salts. In some embodiments of the invention, the water-soluble photoinitiator is 4-trimethylaminomethylbenzophenone hydrochloride. In some embodiments, mixtures of the foregoing may be used.

The aqueous phase of the microemulsion may comprise from about 0.05 to about 1 part by weight of a photoinitiator, and in some embodiments from about 0.1 to about 1 part by weight based on 100 parts by weight of total (co)polymerizable species in the microemulsion.

Water-Soluble Thermal Initiators

Water-soluble thermal initiators useful in the invention include those that, on exposure to heat, generate free-radicals that initiate (co)polymerization of the hydrophilic monomer(s), the oleophilic monomer(s), the (co)polymerizable oligomer(s) and, when present, the (co)polymerizable surfactant(s), discussed herein. Suitable water-soluble thermal initiators include but are not limited to potassium persulfate, ammonium persulfate, sodium persulfate, and mixtures thereof, oxidation-reduction initiators such as the reaction product of the above-mentioned persulfates and reducing agents such as sodium metabisulfite and sodium bisulfite; and 4,4'-azobis(4-cyanopentanoic acid) and its soluble salts (e.g., sodium, potassium). In some embodiments, the water-soluble thermal initiator is ammonium persulfate. Mixtures of two or more of the foregoing may also be used.

Typically, water-soluble thermal initiators are used at temperatures ranging from about 50° C. to about 70° C., while oxidation-reduction-type initiators are used at temperatures of from about 30° C. to about 50° C. Water-soluble thermal initiators may comprise from about 0.05 to about 1 part by weight and in some embodiments from about 0.1 to about 1 part by weight based on 100 parts by weight of (co)polymerizable species in the microemulsion composition.

Water-Soluble Electrolytes

The electrical conductivity of the PSAs of the invention is accomplished by inclusion of a water soluble electrolyte. Electrolytes useful in the present invention include organic chloride electrolytes which facilitate electrical conductivity for the resulting PSA of the invention. Moreover, the organic chloride electrolytes, when paired with a miscible humectant, provide the resulting PSA's with an ability to resist and even avoid a severe reduction in electrical conductivity upon the loss of water or moisture from the finished PSA. In embodiments of the invention, up to about 10 parts by weight of organic chloride electrolyte can be present. In some embodiments, electrolyte may be included at a concentration ranging from about 0.5 parts by weight to about 5 parts by weight based on 100 parts by weight of the total aqueous phase of the microemulsion.

In embodiments of the invention, the organic chloride electrolyte comprises one or more onium chloride. In some embodiments, the onium chloride comprises at least one ammonium chloride (e.g., quaternary ammonium chloride). In some embodiments, the onium chloride comprises at least one phosphonium chloride. In other embodiments, the onium chloride may comprise oxonium chloride or sulfonium chloride. Mixtures of two or more organic chlorides, including the aforementioned onium chlorides, may be used as well. In embodiments where the electrolyte is ammonium chloride, a useful class of organic chlorides is quaternary ammonium chlorides which can include, without limitation, hydroxyethyltrimethylammonium chloride (also known as choline chloride), a ubiquitous naturally occurring salt that is endogenously produced in humans and forms a key component of the lipid bilayer in human cells.

In some embodiments, quaternary ammonium chloride electrolytes include those selected from the aforementioned hydroxyethyltrimethylammonium chloride (choline chloride), as well as benzyltrimethylammonium chloride, benzyltriethylammonium chloride, tetraethylammonium chloride, acetamidopropyl trimethylammonium chloride, lactamidopropyl trimethylammonium chloride, dodecyl trimethylammonium chloride, hexadecyltrimethylammonium chloride, octadecyltrimethylammonium chloride, behenyl trimethylammonium chloride, coconut alkyl trimethylammonium chloride, tetradecyl dimethylbenzylammonium chloride, almond amidopropalkonium chloride, avocadamidopropalkonium chloride, bis-hydroxyethyl tallowmonium chloride, dibehenyldimonium chloride, diocodimonium chloride, didecyldimonium chloride, disoydimonium chloride, ditallowdimonium chloride, PPG-9 diethylmonium chloride, and stearyl ethylhexyldimonium chloride. Combinations of two or more of the foregoing are also contemplated within the scope of the invention.

Humectant

The PSA of the invention comprises one or more humectants. In embodiments of the invention, at least one humectant will be compatible with the organic chloride electrolyte(s) in that the humectant and electrolyte(s) will be miscible within one another. In other aspects, the humectants and the electrolytes will be at least partially miscible in one another. In embodiments of the invention, the humectant is selected to be capable of retaining moisture in the PSA. In aspects of the foregoing embodiments, the humectant is miscible or at least partially miscible with the organic chloride electrolyte to the extent that the humectant is capable of retaining the electrolyte in the PSA after the loss of moisture (e.g., by evaporative loss at low relative humidity) and thereby preventing a sharp degradation of electrical conductivity.

Suitable humectants for use in the conductive PSAs of the present invention include polyhydric alcohols, such as for example, glycerin, propylene glycol, dipropylene glycol, 1,3-butanediol, 1,4-butanediol, trimethylolpropane, ethylene glycol and combinations of two or more of the foregoing. Suitable humectants are generally described by the formula:

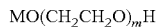

wherein

M is selected from the group consisting of hydrogen and $C_1$ through $C_6$ alkyl; and and m is an integer of about 1 to about 25.

Optional Water Soluble Additives

The microemulsion may optionally further comprise various water-soluble additive(s) associated with the aqueous phase of the microemulsion to produce a polymerized microemulsion PSA having specific properties and/or appearance. Each additive is selected to produce a desired end-product. Examples of useful additives include but are not limited to water-soluble crosslinkers (such as methylene bisacrylamide), plasticizers (such as glycerin and polyalkylene glycols), pH adjusters, other electrolytes, dyes, pigments, pharmaceutically-active compounds, physiologically-active compounds, cosolvents, noncopolymerizable polar oligomers, mixtures thereof, and mixtures of two or more of the foregoing.

Non-(co)polymerizable polar oligomers useful as additives include but are not limited to poly(N-vinylpyrrolidone), polyethylene glycols, poly(oxyethylene) alcohols, poly(ethylimine), and mixtures of two or more of the foregoing. Such oligomers may be added to affect the bulk properties of the resulting polymerized microemulsion PSA, e.g., to impart hydrophilic properties to the material.

Cosolvents may also be included in the microemulsions of the present invention. Such cosolvents include aliphatic alcohols having from about 1 to about 8 carbon atoms (such as glycerin), polyethers (such as those available under the trade designations BUTYL CELLOSOLVE, BUTYL CARBITOL, HEXYL CELLOSOLVE, AND HEXYL CARBITOL, all commercially available from Union Carbide), and mixtures of two or more of the foregoing.

It will be recognized that essentially all organic water soluble additives which are added to the aqueous phase will exhibit a degree of solubility in the organic phase of the microemulsion, and that each additive will have its own distribution ratio between the aqueous phase and the organic phase. Unless otherwise specified, the above-mentioned constituents of the aqueous phase will be found in and will affect the properties of the organic phase also. It is not necessary to the understanding and practice of the present invention to quantify the particular distribution ratio of each and every additive mentioned herein.

Hydrophobic Components

Prior to initiating polymerization, the oil phase of microemulsion compositions of the invention can comprise hydrophobic free-radically (co)polymerizable monomers and/or oligomers suitable for forming a hydrophobic pressure sensitive adhesive homopolymer or copolymer, free radically (co)polymerizable polar monomers, hydrophobic initiator, and optional reactive lipophilic additives.

Hydrophobic Free-Radically (Co)Polymerizable Monomers

Hydrophobic free-radically polymerizable, ethylenically-unsaturated monomers useful in the lipophilic phase of the microemulsions of the present invention include but are not limited to those selected from the group consisting of from about $C_1$ to about $C_{18}$ alkyl esters of acrylic acid, i.e., those esters derived from acrylic acid and from about $C_1$ to about $C_{18}$, provided that such monomers are suitable for forming a hydrophobic polymer having pressure sensitive adhesive properties.

The glass transition temperature ($T_g$) of the polymerized microemulsion PSA can be determined using known techniques, and the $T_g$ of a polymerized microemulsion PSA is determined, in part, by the selection of the hydrophobic monomers used in forming a hydrophobic polymer having pressure sensitive adhesive properties. A $T_g$ of less than about 10° C. will frequently be associated with a hydrophobic polymer having pressure sensitive adhesive properties, and a $T_g$ of less than about 0° C. will more frequently be associated with a hydrophobic polymer having pressure sensitive adhesive properties. Even more frequently, a $T_g$ of less than about −10° C. will be associated with a hydrophobic polymer having pressure sensitive adhesive properties. In some embodiments, alkyl acrylates, including isooctyl acrylate, 2-ethylhexyl acrylate, and n-butyl acrylate, are preferred because of their availability for use and because of the $T_g$ of the resulting hydrophobic polymer formed from such hydrophobic monomers.

The organic phase may further optionally comprise free-radically polymerizable ethylenically-unsaturated comonomers which are copolymerizable with the alkyl acrylate monomers described above in order to modify the glass transition temperature ($T_g$) of the resulting polymerized microemulsion PSA, from that $T_g$ contributed by the hydrophobic monomer(s). Suitable comonomers include styrene, acrylonitrile, and vinyl esters (such as vinyl acetate, vinyl propionate and vinyl neopentanoate, etc.) and combinations thereof. The selection of the comonomer(s) may be dependent on the properties desired of the final solid bicontinuous polymer.

The polymerized microemulsion PSAs of the invention generally comprise from about 5 to about 80 percent by weight of hydrophobic monomers, typically from about 10 to about 70 percent by weight, and in some embodiments from about 12 to about 60 percent by weight based on the total weight of the microemulsion, in order to impart sufficient strength, cohesiveness, and pressure sensitive adhesive properties to the resulting polymerized microemulsion PSA. The actual concentrations of each constituent of the microemulsion can be altered by the skilled practitioner depending on the desired pressure sensitive adhesive properties of the copolymer.

Free-Radically (Co)Polymerizable Polar Monomer

The organic phase of a microemulsion will typically contain a portion of the free-radically polymerizable amphiphilic polar monomers described above because of the partitioning of such organic materials between the aqueous phase and the organic phase of a microemulsion, as described previously. Those skilled in the art will appreciate that each monomer will exhibit its own distribution ratio, the enumeration of which is not necessary for the understanding and practicing of the present invention.

Hydrophobic Initiators

The oil phase of the microemulsion may optionally further comprise an hydrophobic free-radical polymerization initiator. In some embodiments, the initiator is selected from the group consisting of thermal initiators, photoinitiators, and mixtures of the foregoing.

Hydrophobic Photoinitiators

Useful hydrophobic photoinitiators generally include those that generate free radicals on exposure to electromagnetic (usually ultraviolet) radiation which initiate the (co)polymerization of the hydrophilic monomer(s) and/or oligomer(s), the oleophilic monomer(s), and (co)polymerizable surfactant. Useful photoinitiators include, but are not limited to: (1) mixtures of Michler's ketone and benzil or benzophenone, preferably in a weight ratio of about 1:4; (2) coumarin-based photoinitiator systems as described in U.S. Pat. No. 4,289,844, incorporated by reference herein; and (3) systems based on dimethoxyphenylacetophenone and/or diethoxyacetophenone.

Hydrophobic photoinitiators are initially included in the microemulsions as part of the organic phase. On irradiation, the free-radicals thus generated effect (co)polymerization of monomers in both the aqueous and the organic phases, as well as copolymerization of any (co)polymerizable surfactant. In some embodiments, the organic phase of a microemulsion will, comprise from about 0.01 to about 5 parts by weight of an oil soluble photoinitiator, based on 100 parts by weight of total (co)polymerizable species in the microemulsion.

Optional Hydrophobic Thermal Initiators

Hydrophobic thermal initiators may optionally be used in the preparation of the bicontinuous polymers of the present invention subsequent to the photopolymerization step as described above in order to complete the polymerization reaction.

Useful hydrophobic thermal initiators include those that, on exposure to heat, generate free radicals which initiate (co)polymerization of the hydrophilic monomer(s), oligomer(s) the oleophilic monomer(s), and, when present, the polymerizable surfactant, as detailed below. Suitable hydrophobic thermal initiators include but are not limited to those selected from the group consisting of azo compounds such as 2,2'-azobis(isobutyronitrile), available under the trade designation VAZO 64 from Dupont; 2,2'-azobis(2,4-dimethylpentanenitrile), commercially under the trade designations VAZO 52; peroxides such as benzoyl peroxide and lauroyl peroxide; and mixtures of two or more of the foregoing.

The organic phase of a microemulsion may comprise from about 0 to about 5 parts by weight of an hydrophobic thermal initiator, typically about 0.05 to about 5 parts by weight, and in some embodiments about 0.1 to about 5 parts, based on 100 parts of total weight of (co)polymerizable compounds in the microemulsion.

Optional Reactive Lipophilic Additives

Microemulsions may further comprise one or more additional free-radically reactive constituents, including, but not limited to hydrophobic crosslinking agents, chain transfer agents, and mixtures thereof. Such additional components will be present in the oil phase of the microemulsion. Examples of useful crosslinking agents include but are not limited to those selected from the group consisting of divinylbenzene; about $C_4$ to about $C_8$ alkyl diacrylates such as 1,4-butanediol diacrylate, 1,6-hexanediol diacrylate, 1,8-octanediol diacrylate; and mixtures thereof. In some embodiments, the crosslinking agent is 1,6-hexanediol diacrylate. Crosslinking agent, if added, changes the physical properties, such as cohesive strength, of the final polymer.

The oil phase may optionally further comprise about 0 to about 10 or more, parts by weight crosslinker; typically about 0.1 to about 2 parts by weight, based on 100 parts by weight of the total oil phase. The amount of crosslinker used will determine the physical properties of the polymer, such as its solubility (or insolubility) in certain solvents, its modulus and its internal strength.

The microemulsion may further comprise a chain transfer agent soluble in the oil phase. Examples of useful chain transfer agents include carbon tetrabromide, alcohols, mercaptans, and mixtures thereof. In some embodiments, the chain transfer agent is isooctylthioglycolate. The oil phase may comprise up to about 0.5 parts by weight of a chain transfer agent, typically about 0.01 to about 0.5 parts by weight, and in some embodiments from about 0.05 parts by weight to about 0.2 parts by weight, based upon 100 parts by weight of the total oil phase.

Optional Nonreactive Hydrophobic Additives

The microemulsion may optionally further comprise one or more nonreactive hydrophobic additives. A variety of nonreactive hydrophobic additives may be included in the microemulsion. These materials are added to produce a final polymer system with specified physical properties or appearance. Examples of such optional additives include but are not limited to those selected from the group consisting of plasticizers, such as one of the phthalate esters well-known in the art. The oil phase may optionally further comprise about 0 to about 20 parts by weight of a plasticizer, in some embodiments from about 5 to about 20 parts by weight and typically from about 8 to about 15 parts by weight based on 100 parts by weight of the oil phase.

Surfactants

Nonionic and ionic (anionic and cationic) surfactants may be employed in the present invention. The surfactant(s) can be copolymerizable with the monomers present in the microemulsion or the surfactant can be non-(co)polymerizable. In some embodiments, the surfactant(s) are (co)polymerizable so that the resulting polymerized microemulsion is less sensitive to water. When resistance to water is not required, lower costing non-(co)polymerizable surfactants may be used.

Nonionic Surfactants

Typically, nonionic surfactants are condensation products of an organic aliphatic or alkylaromatic hydrophobic compound and an alkylene oxide, such as ethylene oxide, which is hydrophilic. Hydrophobic compounds having a carboxy, hydroxy, amido, or amino group with a free hydrogen present can usually be condensed with ethylene oxide to form a nonionic surfactant. The length of the ethylene oxide chain of the condensation product can be adjusted to achieve the desired balance between the hydrophobic and hydrophilic elements (Hydrophilic-Lipophilic Balance or HLB). The HLB of a surfactant is an expression of the balance of the size and strength of the hydrophilic (water-loving or polar) and the lipophilic (oil-loving or non-polar) groups of the surfactant. The useful HLB of nonionic surfactants for the present invention to prepare microemulsions is from about 6 to about 19, typically from about 9 to about 18, and in some embodiments from about 10 to about 16. Useful nonionic surfactants include non-(co)polymerizable nonionic surfactants, ethylenically-unsaturated copolymerizable nonionic surfactants, and mixtures thereof.

Non-(Co)Polymerizable Nonionic Surfactants

Particularly suitable nonreactive nonionic surfactants include condensation products of a higher aliphatic alcohol, such as a fatty alcohol, containing from about 8 to about 20 carbon atoms, in a straight or branched chain configuration, condensed with about 3 to about 100 moles, typically about 5 to about 40 moles, in some embodiments about 5 to about 20 moles of ethylene oxide to achieve the above defined HLB. Examples of such nonionic ethoxylated fatty alcohol surfactants are those available under the trade designations TERGITOL 15-S from Union Carbide and BRIJ surfactants from ICI. TERGITOL 15-S Surfactants include $C_{11}$-$C_{15}$ secondary alcohol polyethyleneglycol ethers. BRIJ 58 Surfactant is Polyoxyethylene(20) cetyl ether, and BRIJ 76 Surfactant is polyoxyethylene(10) stearyl ether.

Other suitable nonreactive nonionic surfactants include polyethylene oxide condensates of one mole of alkyl phenol containing from about 6 to 12 carbon atoms in a straight or branched chain configuration, with about 3 to about 100 moles, typically about 5 to about 40 moles, in some embodiments about 5 to about 20 moles of ethylene oxide to achieve the above defined HLB. Examples of nonreactive nonionic surfactants are those available under the trade designations IGEPAL CO and CA series from Rhone-Poulenc. IGEPAL CO surfactants include nonylphenoxy poly(ethyleneoxy) ethanols. IGEPAL CA surfactants include octylphenoxy poly(ethyleneoxy) ethanols.

Another group of usable nonreactive nonionic surfactants include block copolymers of ethylene oxide and propylene oxide or butylene oxide with HLB values from about 6 to about 19, typically from about 9 to about 18, and in some embodiments from about 10 to about 16. Examples of such nonionic block copolymer surfactants are the PLURONIC and TETRONIC series of surfactants from BASF. PLURONIC surfactants include ethylene oxide-propylene oxide block copolymers. TETRONIC surfactants include ethylene oxide-propylene oxide block copolymers.

Other satisfactory nonreactive nonionic surfactants include but are not limited to sorbitan fatty acid esters, polyoxyethylene sorbitan fatty acid esters and polyoxyethylene stearates having HLBs from about 6 to about 19, typically from about 9 to about 18, and in some embodiments from about 10 to about 16. Examples of such fatty acid ester nonionic surfactants are those available under the trade designations SPAN, TWEEN, and MYRJ surfactants from ICI. SPAN surfactants include $C_{12}$-$C_{18}$ sorbitan monoesters. TWEEN surfactants include poly(ethylene oxide) $C_{12}$-$C_{18}$ sorbitan monoesters. MYRJ surfactants include poly(ethylene oxide) stearates.

Ethylenically-Unsaturated Copolymerizable Nonionic Surfactants

Suitable nonionic surfactants for incorporation in polymerizable microemulsion compositions of the invention include ethylenically-unsaturated copolymerizable nonionic surfactants including but not limited to those falling within the general formula:

$$R\text{—}O\text{—}(R'O)_m\text{—}(EO)_{(n-1)}\text{—}CH_2CH_2OH$$

where:
R is alkenyl ($C_2$-$C_{18}$), acrylyl, acrylyl ($C_1$-$C_{10}$) alkylmethacrylyl, methacrylyl ($C_1$-$C_{10}$) alkyl, vinylphenyl and vinylphenylene ($C_1$-$C_6$) alkyl;
R'O is bivalent alkyleneoxy groups derived from epoxy compounds having from two to four carbon atoms (e.g., ethylene oxide, propylene oxide, butylene oxide and combinations);
E is a bivalent ethylene radical;
m and n can be the same or different, each representing an integer in the range from about 5 to about 100 with the ratio of m/n ranging from about 20:1 to about 1:20.

For the foregoing surfactants, varying the ratio of m and n will vary the HLB of the polymerizable surfactant. In embodiments of the invention, the HLB for the nonionic surfactant(s) ranges from about 6 to about 19, typically from about 9 to about 18, and in some embodiments from about 10 to about 16. Examples of suitable copolymerizable nonionic surfactants are the alkylene polyalkoxy ethanol surfactants available from PPG Industries under the trade designations MAZON BSN 185, 186 and 187. MAZON BSN surfactants include alkylene polyalkoxy ethanol.

Anionic Surfactants

Anionic surfactants include a hydrophobic moiety selected from ($C_6$-$C_{20}$) alkyl, alkylaryl, and alkenyl groups and an anionic group selected from sulfate, sulfonate, phosphate, polyoxyethylene sulfate, polyoxythylene sulfonate, polyoxethylene phosphate and the alkali metal salts, ammonium salts, and tertiary amino salts of such anionic groups. In some embodiments, a useful ethylenically-unsaturated (co)polymerizable surfactant includes ($C_2$-$C_{18}$) alkenyl polyoxypropylene or ($C_2$-$C_{18}$) polyoxybutylene as a hydrophobic moiety and an anionic group of polyoxyethylene sulfate to prepare microemulsions.

In some embodiments of the invention, nonreactive anionic surfactants and/or ethylenically-unsaturated copolymerizable anionic surfactants can be used, as discussed herein.

Nonreactive Anionic Surfactants

Nonreactive anionic surfactants suitable for use in the present invention include alkyl or alkylaryl sulfates or sulfonates ($C_6$ to $C_{20}$) such as sodium lauryl sulfate (e.g., commercially available under the trade designation POLYSTEP B-3 from Stepan Co. of Northfield, Ill.) and sodium dodecyl benzene sulfonate, (e.g., commercially available under the trade designation SIPONATE DS-10 from Rhone-Poulenc of Cranbury, N.J.); polyoxyethylene ($C_6$ to $C_{20}$) alkyl or alkylphenol ether sulfates with the ethylene oxide repeating unit in the surfactant below about 30 units, typically below about 20 units and in some embodiments below about 15 units, such as POLYSTEPA B1 commercially available from Stepan Co. and ALIPAL EP110 and 115 from Rhone-Poulenc; ($C_6$ to $C_{20}$) alkyl or alkylphenoxy poly(ethyleneoxy)ethyl monoesters and di-esters of phosphoric acid and its salts, with the ethylene oxide repeating unit in the surfactant below about 30 units, typically below about 20 units, and in some embodiments below about 15 units, such as those commercially available under the trade designations GAFAC PE-510 and GAFAC RE-610 from GAF of New York, N.Y.

Ethylenically-Unsaturated Copolymerizable Anionic Surfactants

In embodiments of the invention, anionic surfactants for incorporation in the microemulsion compositions include but are not limited to ethylenically-unsaturated copolymerizable surfactants of the formula:

$$R_1-O-(R_2O)_m-(EO)_{n-1}-CH_2CH_2X$$

where:
$R_1$ is $C_2$ to $C_{18}$ alkenyl, acrylyl, acrylyl ($C_1$ to $C_{10}$) alkyl, methacrylyl, methacrylyl ($C_1$ to $C_{10}$) alkyl, vinylphenyl and vinylphenylene ($C_1$ to $C_6$) alkyl;
$R_2O$ is selected from the group consisting of bivalent alkyleneoxy groups derived from epoxy compounds having more than two carbon atoms, preferably three or four carbon atoms, such as propylene oxide and butylene oxide and mixtures of such alkyleneoxy groups;
E is a bivalent ethylene radical;
m and n can be the same or different, each representing an integer in the range from about 5 to about 100 with the ratio of m/n ranging from about 20:1 to about 1:20; and
X is an anionic group selected from the group consisting of sulfonate, sulfate, phosphate, and alkali metal salts or ammonium salts or tertiary amino salts of such anionic groups.

It will be understood that varying the ratio of m and n will vary the HLB of the polymerizable surfactant. The HLB for the anionic copolymerizable surfactants of the present invention, exclusive of the X-group, is typically from about 3 to about 16. One example of a suitable copolymerizable anionic surfactant according to the above formula is that available under the trade designation MAZON SAM 211, commercially available from PPG Industries, Inc.

Cationic Surfactants

Cationic surfactants can be useful in embodiments of the present invention. Useful cationic surfactants include quaternary ammonium salts, especially those in which at least one higher molecular weight group and two or three lower molecular weight groups are linked to a common nitrogen atom to produce a cation, the electrically-balancing anion being selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing from about 10 to about 20 carbon atoms, and the lower molecular weight substituents may be lower alkyl of from about 1 to about 4 carbon atoms, such as methyl or ethyl, which may be substituted, as with hydroxy, in some instances. One or more of the substituents may include an aryl moiety or may be replaced by an aryl, such as benzyl or phenyl. Possible lower molecular weight substituents include lower alkyls of from about 1 to about 4 carbon atoms, such as methyl and ethyl, substituted by lower polyalkoxy moieties such as polyoxyethylene moieties, bearing a hydroxyl end group, and falling within the general formula:

$$-R_3(CH_2CH_2)_{(n-1)}CH_2CH_2OH$$

where:
$R_3$ is a $C_1$ to $C_4$ divalent alkyl group bonded to the nitrogen; and
n represents an integer of about 1 to about 15.

Alternatively, one or two lower polyalkoxy moieties having terminal hydroxyls may be directly bonded to the quaternary nitrogen instead of being bonded to it through the previously mentioned lower alkyl.

Specific examples of quaternary ammonium halide surfactants suitable for use in the present invention include methyl-bis(2-hydroxyethyl)coco-ammonium chloride or oleyl-ammonium chloride, such as those commercially available under the trade designations ETHOQUAD C/12 and O/12, respectively. Additionally, methyl polyoxyethylene (15) octadecyl ammonium chloride may be used, including that available under the trade designation ETHOQUAD 18/25 from Akzo Nobel Chemicals Inc. of Chicago, Ill. Combinations of two or more of the foregoing may also be used.

Thickening Agents

Thickening agents useful in microemulsions according to the present invention include hydrophilic polymers formed partially or completely from acrylic acid monomer. In some embodiments, homopolymers of acrylic acid are useful, although hydrophilic copolymers of acrylic acid, typically those containing at least about 20%, and in some embodiments at least 80%, residues of acrylic acid, are also useful. The molecular weight of such thickening agents may be between from about 200,000 and about 800,000, with some embodiments being between about 400,000 and about 700,000.

Adhesive Hydrogels

In embodiments, the PSAs of the invention may be in the form of an adhesive hydrogel. Such a hydrogel may, for example, be an acrylate based single phase PSA. In some embodiments, the hydrogel can be prepared with an adhesive precursor resulting from the reaction of acrylic acid, 2-hydroxyethyl methacrylate tetrakis (hydroxymethyl) phosphonium chloride, butylene glycol, glycerol, water, initiator (e.g., IRGACURE 2959 initiator) and polyethylene glycol(400) diacrylate. The unreacted (e.g., non-polymerized) precursor may be coated onto a release liner as substrate. Polymerization is then induced in the coated microemulsion by exposing the precursor to electromagnetic radiation (e.g., ultraviolet light) for a set period of time (e.g., 10 minutes or less) to initiate the polymerizations reaction and to thereby convert the coated precursor into a conductive adhesive.

Biomedical Articles

In embodiments of the invention, the aforementioned conductive PSAs may be used as components of biomedical articles such as, for example, biomedical electrodes.

Biomedical Electrodes

Biomedical electrodes employing polymerized, electrolyte-containing, PSA's are useful for diagnostic (including monitoring) and therapeutic purposes. In a basic form, a biomedical electrode comprises a conductive medium capable of contacting mammalian skin and a means for electrical communication between the conductive medium and electrical diagnostic, therapeutic, or electrosurgical equipment. In embodiments, the conductive medium capable of contacting mammalian skin comprises the conductive adhesive compositions described herein.

Figure 2:
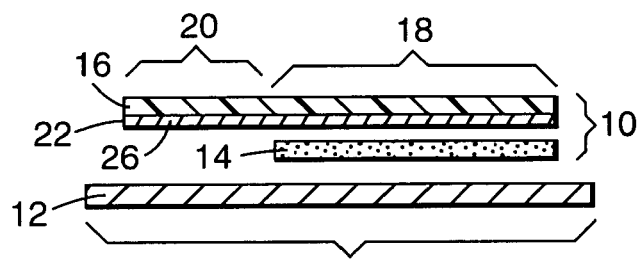
FIG. 2 is a cross-sectional view of the biomedical electrode of FIG. 1.

Referring now to the drawings, FIGS. 1 and 2 illustrate an electrode 10 with a release liner 12. The electrode 10 may be a disposable diagnostic electrocardiogram (ECG or EKG) or a transcutaneous electrical nerve stimulation (TENS) electrode, for example. Electrode 10 includes a field 14 of biocompatible conductive adhesive, as described above, for contacting mammalian skin following the removal of protective release liner 12. The adhesive field 14 holds the electrode 10 to the skin of the patent while also conducting electricity therethrough for therapeutic, diagnostic or monitoring purposes. The conductive adhesive field 14 includes first and second major surfaces. Electrode 10 includes means for electrical communication comprising a conductor member 16 having a conductive interface portion 18 contacting a first major surface of conductive adhesive field 14 and a tab portion 20 extending beyond conductive adhesive field 14 for mechanical and electrical contact with electrical instrumentation (not shown) such as by means of an alligator clip or the like. Side 22 of the conductor member 16 includes a conductive layer 26 coated thereon and contacting the first major surface of the conductive adhesive field 14. The second major surface of the conductive adhesive field 14 adheres the electrode 10 to the skin following the removal of the release liner 12.

In some embodiments, conductor member 16 can comprise a strip of polymeric material such as a polyester film. The conductor member 16 may have a thickness within the range from about 0.05 mm to about 0.2 mm, and a conductive layer 26 coated over side 22. The conductive layer 26 may comprises silver/silver chloride at a dried coating thickness of between about 2.5 micrometers and about 12 micrometers. In some embodiments, the coating thickness is about 5 micrometers. Suitable polyester films for use as a conductor member 16 include those commercially available under the trade designation SCOTCHPAK from 3M Company of St. Paul, Minn. as well as those available under the designation MELINEX 505-300, 329, or 339 film from ICI Americas of Hopewell, Va. and coated with a silver/silver chloride ink commercially available under the designation "R-300" commercially available from Ercon, Inc. of Waltham, Mass.

The conductor member 16 for a TENS electrode can be made of a nonwoven web of fibers. One such web comprises polyester/cellulose fibers such as those commercially available under the trade designation MANNIWEB from Lydall, Inc. of Troy, N.Y. and having a conductive layer 26 of carbon ink commercially available under the trade designation "SS24363" ink from Acheson Colloids Company of Port Huron, Mich. To enhance mechanical contact between an electrode clip (not shown) and conductor member 16, an adhesively-backed polyethylene tape can be applied to tab portion 20 on the outermost side of the conductor member 16 (e.g., opposite side 22). A surgical tape commercially available from 3M Company under the designation BLENDERM can be employed for this purpose.

In some embodiments, the conductor member 16 can be provided in a multi-layered construction comprising a nonconductive, flexible polymeric film having a sulfur-reactive surface, a metallic layer deposited on and interacting with the sulfur-reactive surface and an optional metallic halide layer, as described in U.S. Pat. No. 5,506,059, the entire disclosure of which is incorporated herein by reference thereto. The conductive interface portion 18 of conductor member 16 comprises a metallic layer deposited on a sulfur-reactive surface on at least the side of the polymeric film substrate that faces conductive adhesive field 14.

In other embodiments, conductor member 16 can be a multi-layered construction comprising a nonconductive, flexible polymeric film, an electrically conductive layer, and a thin, conformable depolarizing layer of inorganic oxide (e.g., manganese dioxide). Alternatively, conductor member 16 can be a multilayered construction of film with electrically conductive and depolarizing layers blended together. Both of the foregoing embodiments can be constructed according to the teaching of U.S. Pat. No. 5,505,200, the entire disclosure of which is incorporated herein by reference thereto. The conductive interface portion of conductor member 16 comprises an electrically conductive layer coated on at least the side of polymeric film facing conductive adhesive field 14 and the thin, depolarizing layer coated on the electrically conductive layer and contacting field 14.

Non-limiting examples of biomedical electrodes that can use the conductive PSAs of the present invention include electrodes disclosed in U.S. Pat. Nos. 4,524,087; 4,539,996; 4,554,924; 4,848,353; U.S. Pat. No. 4,846,185; U.S. Pat. No. 4,771,713; U.S. Pat. No. 4,715,382; U.S. Pat. No. 5,012,810; and U.S. Pat. No. 5,133,356; the entire disclosures of which are incorporated herein by reference thereto.

In some embodiments, means for electrical communication can comprise an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, a polymerized PSA of the present invention, containing an electrolyte, can reside as a field of conductive adhesive on a biomedical electrode for diagnostic (including monitoring), therapeutic, or electrosurgical purposes.

Another type of diagnostic procedure that can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.), the entire disclosure of which is incorporated herein by reference thereto. The polymerized PSA of the present invention can be used as the ionically conductive medium in any of the embodiments shown therein. In some embodiments, the polymerized PSA of the present invention is used as the field of conductive adhesive in a biomedical electrode according to the embodiment shown, for example, in FIGS. 2, 3, and 4 of U.S. Pat. No. 5,012,810.

Figure 3:
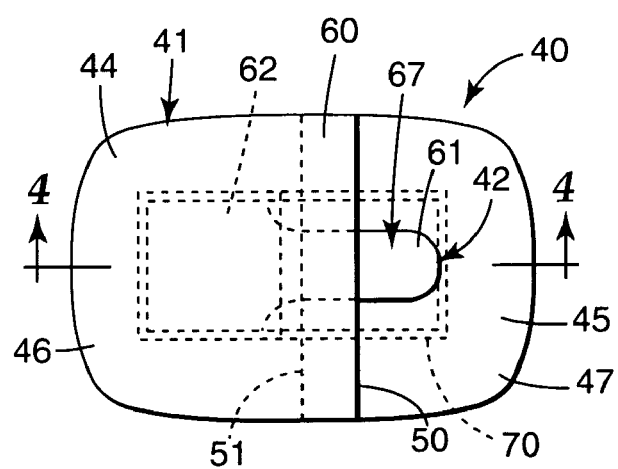
FIG. 3 is a top plan view of an embodiment of a monitoring biomedical electrode useful for longer term diagnosis or monitoring of heart conditions, the electrode including a conductive adhesive according to the present invention.
Figure 4:
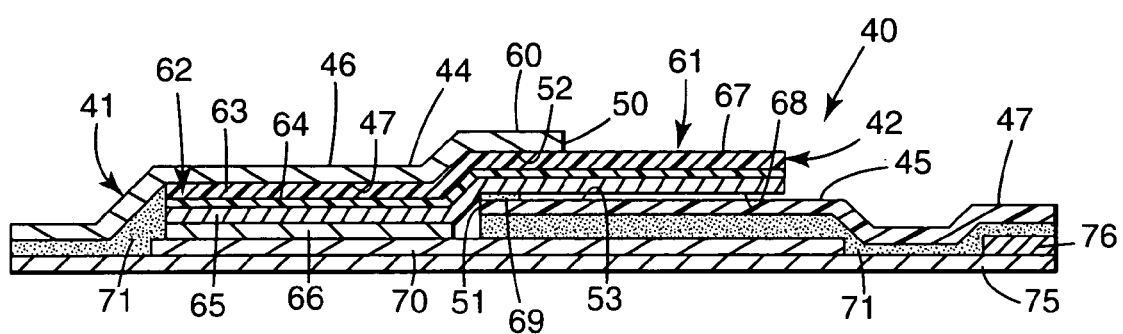
FIG. 4 is a cross-sectional view of the monitoring biomedical electrode of FIG. 3.

Referring to FIGS. 3 and 4 herein, another embodiment of a biomedical electrode is provided in the form of electrode 40 which includes an insulator construction 41, and a conductor member 42. Insulator construction 41 has first section 44 and second section 45 which, together, define opposite sides 46 and 47 of the insulator construction 41. As seen in FIG. 3, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. As used herein, "substantially parallel" does not mean that the sections 44 and 45 are precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment, conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of U.S. Pat. No. 5,506,059 described above.

The pad portion 62 of member 42 comprises the portion of the metallic film facing conductive adhesive field 70, optionally with metallic halide layer 66 contacting the field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 1 and 2 in order to enhance mechanical contact.

In general, electrode 40 is constructed such that tab portion 61 of conductor member 42 projects through seam 60 and over a portion of surface or side 46. As a result, as seen in FIGS. 3 and 4, pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 4, lower surface 68 of tab portion 61 is shown adhered in position to section 45, by means of double-stick tape strip 69. That is, adhesion in FIG. 1 between the tab portion 61 and section 45 is by means of adhesive 69 underneath tab portion 61, rather than on top as shown in FIG. 4.

In the electrode 40 of FIG. 4, a conductive adhesive field 70 comprises a PSA according to the present invention which is positioned generally underneath conductive member 42. Optionally, conductive adhesive field 70 will be surrounded by a biocompatible skin adhesive field 71 applied to insulator construction 41 on the side with pad portion 62 thereon. In some embodiments, the conductive adhesive 70 can comprise hydrophobic bulk properties. In such cases, the field 71 can be eliminated. In some embodiments, the biocompatible skin adhesive field 71 or can comprise a non-conductive polymerized PSA similar to the conductive adhesives described herein but without the organic chloride electrolyte. Release liner 75 is positioned against that side of electrode 40 which also includes optional skin adhesive 71, conductive adhesive 70 and pad portion 62 thereon. Spacer 76 is positioned between release liner 75 and a portion of insulator construction 41, to facilitate the separation.

Any of a variety of materials may be utilized for release liners (e.g., the release liners 12, 75) on the foregoing electrodes. On such release liner, for example, comprises a polymer (e.g., a polyester or polypropylene material) coated with a silicone release type coating to render the liner readily separable from the skin adhesive and conductive adhesive. In some embodiments, a liner comprising a polymer such as a polyester or polypropylene material, coated with fluorochemical based coating are useful and are readily separable from the skin adhesive and conductive adhesive. Release liners suitable for use with the foregoing electrodes can include fluorochemical release coatings according to the disclosures in pending U.S. patent application Ser. No. 11/027,612 (filed Dec. 28, 2004), Ser. No. 11/027,605 (filed Dec. 28, 2004), Ser. No. 11/027,633 (filed Dec. 28, 2004), Ser. No. 11/027,606 (filed Dec. 28, 2004) and Ser. No. 11/027,604 (filed Dec. 28, 2004). Suitable commercially available fluorochemical based polyester liners are available from 3M Company of St. Paul, Minn. under the trade designations SCOTCHPAK 1020 SCOTCHPAK 1022, SCOTCHPAK 9741.

Regarding the sections 44 and 45 of the insulator construction 41, a flexible, strong and relatively thin material is typically used to provide the electrode in a construction that is comfortable to the user. In some embodiments, the material can be a foamed polymer such as, for example, polyethylene foam. Other suitable materials include non-woven pads (e.g., polyester non-woven pads), paper, and transparent films. Nonlimiting examples of transparent films include polyester film such as those commercially available under the trade designation MELINEX from DuPont/Teijin Films, Hopewell, Va. having a thickness of 0.05 mm and a surgical tape commercially available from 3M Company as TRANSPORE unembossed tape. In some embodiments, the materials comprise non-woven pads made from melt blown polyurethane fiber, which exhibit exceptional flexibility, stretch recovery and breathability. Suitable melt blown polyurethane materials that may be used in insulator construction 41 in electrodes according to the present invention are generally described in European Patent Publication 0 341 875 (Meyer) and corresponding U.S. Pat. No. 5,230,701 (Meyer et al.), the entire disclosures of which are incorporated herein by reference thereto.

Optionally the insulator construction can include a skin adhesive on its surface contacting the remainder of the electrode 40.

In embodiments of the invention, web materials (melt blown polyurethanes) used in insulator construction 41 can have a web basis weight from about 60 to about 140 $g/m^2$ (e.g., about 120 $g/m^2$). Such materials will also have a suitable tensile strength and moisture vapor transmission rate. Suitable moisture vapor transmission rates include those in the range from about 500 to about 3000 grams water/$m^2$/24 hours, and in some embodiments from about 500 to about 1500 grams water/$m^2$/24 hours, when tested according to ASTM E96-80 at 21° C. and 50% relative humidity. In some embodiments, the material has a stretch recovery of at least about 85%, in all directions, after stretch of 50%.

While the insulator construction described herein can be made to have any of a variety of dimensions and may be made in virtually any size or shape, it will be appreciated that conventional biomedical electrodes are relatively small devices. In embodiments of the electrodes described herein, the dimensions of the insulator construction typically will range from about 3.5 to about 4.5 cm in a first dimension (e.g., width) and from about 5.5 cm to about 10 cm in a second dimension (e.g., length). Depending on the materials used, a thickness of about 200 to 600 micrometers typically provides adequate strength and a low relief or profile, suitable for most applications.

Regarding the adhesive 69, any of the acrylate ester adhesives in double stick tape form may be used. In some embodiments, the adhesive 69 can be the same adhesive as described herein for the skin adhesive but having an inherent viscosity from about 1.3 to about 1.45 dl/g. For the field 70 of conductive adhesive, conductive adhesives such as those described above as useful for field 14 of conductive medium are preferred.

It will be appreciated that the dimensions of the various layers, and their conformation during association, are not to scale in any of the various Figures. In fact features may be shown in the Figures in a somewhat exaggerated manner in order to better illustrate the features of the depicted construction(s) and thereby facilitate a better understanding of the construction. In general, an overall substantially flat appearance with only a very minor "s" type bend in the conductive member 42 is accommodated by the arrangement, despite the multilayered construction of member 42.

Other examples of biomedical electrodes which can use the conductive PSAs of the present invention include the electrodes disclosed in U.S. Pat. Nos. 4,527,087; 4,539,996; 4,554,924; 4,848,353 (Engel); U.S. Pat. No. 4,846,185 (Carim); U.S. Pat. No. 4,771,713 (Roberts); U.S. Pat. No. 4,715,382 (Strand); U.S. Pat. No. 5,133,356 (Bryan et al.), the entire disclosures of which are incorporated herein by reference thereto. Methods of making such electrodes are disclosed in such patents, except that polymerized PSAs of the invention can be substituted for the field of conductive adhesive and optionally also the field of skin adhesive disclosed in such patents.

EXAMPLES

Embodiments of the invention are further illustrated by the following non-limiting Examples, in which all parts are by weight unless otherwise stated.

Test Methods

For testing purposes electrode pairs were adhered to each other, their layers of bicontinuous adhesive being placed in contact face-to-face. This arrangement is specified in a standard published by the Association for the Advancement of Medical Instrumentation (AAMI) for determining the proper performance for a biomedical electrode used for ECG Disposable Electrodes, specifically the "American National Standard for Pregelled ECG Disposable Electrodes" Association for the Advancement of Medical Instrumentation (1984), the disclosure of which is incorporated by reference, for testing methods and conditions for minimum standards. The properties of D.C. Offset (less than 100 mV); A.C. Impedance (less than 2 kOhms); Defibrillation Overload Recovery (less than 100 mV, 5 seconds after 4 capacitor discharges) and a rate of change of Residual Polarization Potential (no greater than 1 mV/sec.) were measured for Test Examples and Comparative Examples according to these standard test methods.

Example 1

This example employs an organic chloride electrolyte in a conductive adhesive used in tab style electrodes. A microemulsion was prepared for use as a conductive adhesive according to the invention. The microemulsion was prepared in the manner generally disclosed in coassigned U.S. Pat. No. 6,709,716 issued Mar. 23, 2004 to Uy et al. More specifically, a first mixture was formed by mixing quantities of two monomers, namely 14 grams of acrylic acid as a hydrophilic monomer with 14 grams of isooctyl acrylate as a hydrophobic monomer that was commercially obtained from e.g., Atofina Chemicals, Inc. of Philadelphia, Pa. To this was added 7 grams of a surfactant, commercially available under the trade designation BRIJ 98 from Uniqema of New Castle, Del.; and 3 grams of a surfactant, commercially available under the trade designation HETOXOL OL35 from Global Seven of Franklin, N.J. Then, 0.3 grams of photoinitiator, commercially available under the trade designation IRGACURE 2959, from Ciba Gigy Corp., was added to complete a first mixture.

A second mixture was then prepared by mixing 22 grams water; 8 grams choline chloride from Spectrum Chemicals of Brunswick, N.J.; 10 grams glycerol; 25 grams of butylene glycol, both from Sigma Chemicals of Milwaukee, Wis.

The first and second mixtures were combined together to form a microemulsion. To the microemulsion, 0.2 grams a hydrophobically modified polyacrylate prepared from acrylic acid monomer, commercially available under the trade designation of PEMULEN TR-2, obtained from Noveon Inc. of Cleveland, Ohio, was added as a viscosity modifier and 0.2 grams of polyethylene glycol (400) diacrylate obtained from Sartomer Company, Inc of Exton, Pa. was added as a crosslinking agent. After the addition, the microemulsion remained clear and stable and the viscosity increased to approximately 200 cp, readily processable using conventional techniques.

The thickened microemulsion was then coated using a knife coater onto a release liner as substrate. The knife was set so that a 0.64 mm (25 mil) thick coating was obtained. Polymerization was induced in the coated microemulsion by exposure to ultraviolet radiation using a 350 Blacklight, commercially available from Sylvania of Danvers, Mass. A total dose of 1800 mJ/cm$^2$ was applied over approximately 7 minutes, forming a conductive, bicontinuous adhesive. This conductive adhesive had an excellent adhesion to human skin.

Several 1.0 square centimeter swatches of this adhesive were bonded to a conductive silver/silver chloride ink backing on one side and to a release liner on the other side. The backing was larger than the adhesive swatch (2 cm×1 cm) leaving 1 square cm as a tab for electrical contact. The backing was made by coating a silver/silver chloride conductive ink solution commercially available under the trade designation "R300", from Ercon Inc. of Waltham, Mass., onto a polymeric backing made from 0.1 mm thick polyester film commercially available under the trade designation MELINEX 505 from ICI Films of Hopewell, Va., using a wire-coating procedure. The ink had a solids content of 58%, of which the elemental silver comprised 70%. The carrier solvent for the ink was methyl propyl ketone (MPK). The coated film was then dried at room temperature for 5 minutes followed by drying at 93° C. (200° F.) for 5 minutes.

Comparative Example C1

A microemulsion adhesive was prepared according to the procedure outlined in Example 1 above, with the following changes: four grams of potassium chloride were used in place of choline chloride. 26 grams of water was used, and the surfactant mixture was replaced with 10 grams of BRIJ 97 obtained from Uniqema of New Castle, Del.

Example 1 and Comparative Example C1

Six tab style electrodes were fabricated from the adhesives described in each Example 1 and Comparative Example C1. Three each of the electrode pairs were placed in a 15% R.H. chamber for 18 hours with the adhesive surface exposed while another 3 pairs were not exposed to the 15% R.H. Electrode pairs were prepared from both the unexposed and 15% R.H. exposed samples. These pairs were adhered to each other, their layers of bicontinuous adhesive being placed in contact face-to-face according to the AAMI standard. Each result in Table 1 shows the average test results for 3 pairs of Example 1 and Comparative Example C1, before and after exposure to the 15% R.H.

TABLE 1

| | | Electrode Test: | | | | |
|---|---|---|---|---|---|---|
| | | DC offset (mV) 60 s | $Z_{10}$ (ohms) | SDR after 4 pulses (mV) | SDR slope (mV/s) | $Z_{10}$ (ohms) |
| | | AAMI limit: | | | | |
| Example | | <10 mV | <2000 ohms | <100 mV | <1 mV/s | <2000 ohms |
| 1A | No exposure to 15% R.H. | 0.3 | 57 | 8.7 | −0.3 | 56 |
| 1B | After 15% R.H. exposure | −0.1 | 537 | 14.2 | −0.4 | 516 |
| C1A | No exposure to 15% R.H. | −0.8 | 30 | 8.5 | −0.3 | 31 |
| C1B | After 15% R.H. exposure | −0.4 | 1456 | 32.5 | −1.7 | 1501 |

After equilibrating the adhesive to 15% R.H., the Example 1 electrodes were still electrically viable. The Comparative Example C1B impedance increased by a factor of 50 as opposed to Example 1B (choline chloride) electrode, where the impedance after dry out increased by only a factor of 10. In addition, the C1B electrodes, with potassium chloride, failed the SDR slope test.

Example 2

This example employs organic chloride electrolytes in conductive adhesives used in snap type electrodes which are used for monitoring and longer-term wear. The conductive element has a much smaller footprint than the tab-style electrodes. The electrode construction is described in detail in U.S. Pat. No. 6,709,716 issued Mar. 23, 2004 to Uy et al. Briefly, the biomedical electrode has a nonconductive backing having an opening covered by a snap through which a stud or eyelet protrudes. The snap is secured to the eyelet to provide a point of electrical connection to electrical instrumentation. Covering the eyelet and backing is a field of the polymerized microemulsion PSA of the present invention. A release liner protects the PSA field prior to use. The backing can be made of the same or similar materials as the insulator construction. The eyelet can be a plastic, metallic plated eyelet (such as an ABS plastic eyelet silver-plated and chlorided and commercially available from Micron Products of Fitchburg, Mass.). The snap can be a metallic snap (such as stainless steel eyelet No. 304 commercially available from Eyelets for Industry of Thomason, Conn.). In this type of electrode the polymerized microemulsion PSA of the present invention can serve both as the biocompatible skin adhesive and as the ionically conductive medium in the electrode.

The same adhesive as is described in Example 1 was used to prepare snap-type electrodes. As in Example 1, half of the electrodes were removed from the liner and placed in a chamber at 15% R.H. for 18 hours with the adhesive surface exposed for rapid equilibration with the chamber. The results of electrical testing, according to the AAMI procedure on both sets of electrodes, are shown in Table 2. Each test result represents an average of 3 pairs of electrodes.

Comparative Example C2

Comparative Example C2 used the same snap-type electrode construction as in Example 2, except that choline chloride electrolyte was replaced with potassium chloride as in Comparative Example C1. The AAMI electrical testing data is shown in Table 2. Each test result represents an average of 3 pairs of electrodes.

TABLE 2

| | | Electrode Test: | | | | |
|---|---|---|---|---|---|---|
| | | DC offset (mV) 60 s | $Z_{10}$ (ohms) | SDR after 4 pulses (mV) | SDR slope (mV/s) | $Z_{10}$ (ohms) |
| | | AAMI limit: | | | | |
| Example | | <10 mV | <2000 ohms | <100 mV | <1 mV/s | <2000 ohms |
| 2A | No 15% R.H. Exposure | −0.2 | 225 | 9.8 | −0.2 | 207 |
| 2B | After 15% R.H. Exposure | −0.4 | 1285 | 13.5 | −0.3 | 1347 |
| C2A | No 15% R.H. Exposure | 0 | 279 | 9.3 | −0.2 | 175 |
| C2B | After 15% R.H. Exposure | −0.6 | 3505 | 17.3 | −0.4 | 3503 |

The Example 2B electrodes exhibited a six-fold increase in impedance. None of the electrical characteristics of the electrodes were compromised. The electrodes of Comparative Example C2 failed the impedance test when exposed to a low humidity chamber.

Example 3

Example 3 employed organic electrolytes in conductive adhesives for snap type electrodes converted on release liner where the adhesive perimeter (sandwiched between the electrode backing and the release liner) was exposed to low humidity. Snap-type electrode backings were fabricated as in Example 2 and were converted on release liner using the adhesive synthesized in Example 1. Initial back-to-back electrical testing was conducted according to the AAMI procedure using 12 electrode pairs. Example 3 electrodes on release liner were then aged at 21° C. (70° F.) in two independent chambers maintained at 0% R.H. and 15% R.H. for 30 days. Samples were pulled from both chambers after 10, 20, and 30 days of aging. Back-to-back electrical testing on both sets of electrodes was conducted according to the AAMI procedure on 12 pairs of electrodes at each of these time points. The average results for both sets of Example 3 electrodes are shown below in Table 3A.

Comparative Example C3

A microemulsion was prepared as follows. A first mixture was formed by mixing two hydrophilic monomers, 14 grams of acrylic acid with 14 gram of polyoxyethylene acrylate, commercially available as AM 90G ester from Shin-Nakamura Chemical Co. Ltd. of Wakayama Japan. To this was added 14 grams of isooctyl acrylate in the role of a hydrophobic monomer. To this second mixture was added 18 grams of a surfactant BRIJ 97, available from ICI to form a third mixture. Then 0.5 grams of IRGACURE 2959 initiator, was added to form a fourth mixture. An aqueous mixture was then prepared containing 23 grams water, 1.2 grams KCl and 10 grams of propylene glycol. The aqueous mixture and the fourth mixture were combined together to form a microemulsion. To the microemulsion was added a 17% aqueous polyacrylic acid solution having a molecular weight approximately 550,000, prepared from monomer using standard synthetic techniques. Specifically, polymerization was initiated by the heat activated initiator potassium persulfate, and the reaction was run under a nitrogen atmosphere at 76° C.

When the solution was added to the microemulsion, the microemulsion remained clear and stable and the viscosity increased to approximately 200 cps, readily processable using conventional techniques. The thickened microemulsion was then coated using a knife coater onto a release liner as substrate. The knife was set so that a 25 mil (0.64 mm) thick coating was obtained. Polymerization was induced in the coated microemulsion by exposure to ultraviolet radiation using a 350 Blacklight, commercially available from Sylvania of Danvers, Mass. A total dose of 1800 mJ/cm$^2$ was applied over approximately 7 minutes, forming a conductive, bicontinuous adhesive. This conductive adhesive had an excellent adhesion to human skin.

Snap-type electrode backings were fabricated according to Example 2 and converted on release liner using this adhesive. Initial back-to-back electrical testing was conducted according to the AAMI procedure using 12 electrode pairs. Electrodes on release liner were then aged at 21° C. (70° F.) in two independent chambers maintained at 0% R.H. and 15% R.H. for 30 days. Samples were pulled from both chambers after 10, 20, and 30 days of aging. Back-to-back electrical testing on both sets of electrodes was conducted according to the AAMI procedure on 12 pairs of electrodes at each of these time points. The average results for both sets of Comparative Example C3 electrodes are shown in Table 3B.

TABLE 3A

| | Electrode Test: | | | | |
|---|---|---|---|---|---|
| Example 3 vs. | DC offset (mV) 60 s | $Z_{10}$ (ohms) | SDR after 4 pulses (mV) | SDR slope (mV/s) | $Z_{10}$ (ohms) |
| | | | AAMI limit: | | |
| Comparative Example C3 | <10 mV | <2000 ohms | <100 mV | <1 mV/s | <2000 ohms |
| 3A: Initial - Control | 0.6 | 198 | 5.7 | −0.2 | 165 |
| 3B: 10 days @ 15% RH | 0.9 | 394 | 7.5 | −0.2 | 380 |
| 3C: 20 days @ 15% RH | 1.6 | 855 | 9.5 | −0.3 | 835 |
| 3D: 30 days @ 15% RH | 1.1 | 1241 | 10.9 | −0.3 | 1210 |
| 3E: 10 days @ 0% RH | 0.5 | 378 | 7.9 | −0.2 | 363 |
| 3F: 20 days @ 0% RH | 1.3 | 762 | 8.9 | −0.2 | 739 |
| 3G: 30 days @ 0% RH | 1.2 | 1286 | 10.6 | −0.3 | 1255 |

TABLE 3B

| | Electrode Test: | | | | |
|---|---|---|---|---|---|
| Example 3 vs. | DC offset (mV) 60 s | $Z_{10}$ (ohms) | SDR after 4 pulses (mV) | SDR slope (mV/s) | $Z_{10}$ (ohms) |
| | | | AAMI limit: | | |
| Comparative Example C3 | <10 mV | <2000 ohms | <100 mV | <1 mV/s | <2000 ohms |
| C3A: Initial - Control | 0.5 | 264 | 11.5 | −0.2 | 232 |

TABLE 3B-continued

| | Electrode Test: | | | | |
|---|---|---|---|---|---|
| Example 3 vs. | DC offset (mV) 60 s | $Z_{10}$ (ohms) | SDR after 4 pulses (mV) | SDR slope (mV/s) | $Z_{10}$ (ohms) |
| | | | AAMI limit: | | |
| Comparative Example C3 | <10 mV | <2000 ohms | <100 mV | <1 mV/s | <2000 ohms |
| C3B: 10 days @ 15% RH | 2.3 | 3928 | 19.5 | −0.5 | 3925 |
| C3C: 20 days @ 15% RH | 0.76 | 3874 | 33.2* | −1.2 | 3875 |
| C3D: 10 days @ 0% RH | 1.1 | 3115 | 15.3 | −0.4 | 3067 |
| C3E: 20 days @ 0% RH | 4 | 3933 | 37* | −1.0 | 3934 |

*Several electrode pairs displayed a DCO greater than 2 V at 2 seconds after the SDR pulse Example 4

Example 4 shows the clinical performance of electrodes fabricated from adhesive containing choline chloride and aged for 30 days on liner at 0% and 15% R.H. The clinical performance was measured by the time required to obtain a stable ECG trace after electrode application on the skin.

Materials: Snap-type electrodes were fabricated from the backing, adhesive, and liner materials described in Example 3. One third of the electrodes were sealed in water and air-impermeable pouches, these electrodes served as controls. Another third was aged on liner at 21° C. (70° F.) and 0% R.H. for thirty days and the remaining third was aged on liner at 21° C. (70° F.) and 15% R.H. for thirty days.

The initial impedance was first measured using each Example 4 electrode applied to a subject's arm. One sample of each Example 4 electrode (4A, control; 4B, stored @15% R.H. and 4C, stored @0% R.H.) was applied to each of 4 quadrants on each of 12 subjects' torso. The time to acceptable EKG trace was recorded. Note, that an acceptable trace was required in both leads 1 and 2. The average results (n=48) of the impedance and time to acceptable trace for each Example 4 electrode, under each condition, are shown in Table 4.

TABLE 4

| Example | Impedance (k ohms) | Time to Acceptable Trace (seconds) |
|---|---|---|
| 4A: Control | 50 | 13 |
| 4B: 30 days @ 21° C. + 15% RH | 133 | 29 |
| 4C: 30 days @ 21° C. + 0% RH | 125 | 53 |

Example 5

This Example employed a different organic "onium" electrolyte in conductive adhesives used in snap type electrodes. The electrode construction is identical to the one described in Example 2 with the exception of the adhesive. The adhesive was an acrylate based single phase PSA. The adhesive precursor comprises 15 grams of acrylic acid, 20 grams of 2-hydroxyethyl methacrylate obtained from San Esters Corporation of New York, N.Y.; 11 grams of tetrakis(hydroxymethyl) phosphonium chloride commercially available from Sigma-Aldrich of St. Louis, Mo.; 25 grams 1,3 butylene glycol, 10 grams glycerol, 19 grams water, 0.55 grams IRGACURE 2959 and 0.15 grams polyethylene glycol(400) diacrylate. The precursor was coated using a knife coater onto a release liner as substrate. The knife was set so that a 25 mil (0.64 mm) thick coating was obtained. Polymerization was induced in the coated microemulsion by exposure to ultraviolet radiation using a 350 Blacklight, commercially available from Sylvania of Danvers, Mass. A total dose of 1800 mJ/cm$^2$ was applied over approximately 7 minutes, forming a conductive, bicontinuous adhesive. This conductive adhesive had an excellent adhesion to human skin.

Snap-type electrode backings were fabricated as in Example 2 and converted on release liner using this adhesive.

Comparative Examples C5

Comparative Example C5 used the same electrode construction as in Example 4, except replacing the phosphonium chloride adhesive with a potassium chloride adhesive of the same composition with the following exceptions: 11 grams of the phosphonium chloride was replaced with 4.2 grams potassium chloride and 19 grams water was increased to 25.8 grams.

Example 5 and Comparative Example C5

Electrical testing according to the AAMI procedure was conducted on both sets of electrodes (3 each) for Example 5 and for Comparative Example C5. As in the previous examples, half the electrodes were removed from the liner and placed in a 15% R.H. chamber for 18 hours with the adhesive surface exposed for rapid equilibration with the chamber, while half were not exposed to the 15% R.H. condition. The results are shown in Table 5, below.

TABLE 5

| | | Electrode Test: | | | | |
|---|---|---|---|---|---|---|
| | | DC offset (mV) 60 s | $Z_{10}$ (ohms) | SDR after 4 pulses (mV) | SDR slope (mV/s) | $Z_{10}$ (ohms) |
| | | AAMI limit: | | | | |
| Example | | <10 mV | <2000 ohms | <100 mV | <1 mV/s | <2000 ohms |
| 5A | No 15% R.H. Exposure | −0.1 | 288 | 10.6 | −0.2 | 286 |
| 5B | After 15% R.H. Exposure | 2.9 | 1380 | 12.1 | −0.3 | 1558 |
| C5A | No 15% R.H. Exposure | 0.1 | 156 | 8.4 | −0.2 | 133 |
| C5B | After 15% R.H. Exposure | 0.3 | 3503 | 19.7 | −0.4 | 3515 |

Example 5B electrodes with phosphonium chloride withstood drying out with a six-fold increase in impedance. None of the electrical characteristics of the electrodes were compromised. Comparative Example C5B, the potassium chloride based electrodes, showed a 20-fold increase in impedance and failed the impedance test when exposed to a low humidity chamber.

Although embodiments of the invention have been described in detail, changes and modifications to the described embodiments may be apparent to those skilled in the art, such changes and modifications are contemplated within the spirit and scope of the invention, as set forth in the appended claims.

We claim:

1. A conductive adhesive composition, comprising:
   (a) pressure sensitive adhesive;
   (b) electrolyte comprising water soluble or water dispersible organic chloride; and
   (c) humectant,
   wherein the electrolyte and the humectant are at least partially miscible in one another.

2. The conductive adhesive composition of claim 1 wherein the pressure sensitive adhesive is a bicontinuous composition comprising an aqueous phase and an oil phase.

3. The conductive adhesive composition of claim 2 wherein the bicontinuous composition is derived from a polymerizable microemulsion composition, the microemulsion composition comprising:
   (a) an aqueous phase comprising one or more hydrophilic monomers or oligomers and/or one or more amphiphilic monomers or oligomers in water, the water-soluble or water-dispersible organic chloride, surfactant and humectant;
   (b) an oil phase comprising one or more hydrophobic monomers or oligomers.

4. The conductive adhesive composition as in claim 3, wherein the organic chloride is present in an amount of up to about 20 parts by weight of the total aqueous phase.

5. The conductive adhesive composition as in claim 3, wherein the organic chloride is present in an amount from about 0.5 parts by weight to about 10 parts by weight based on 100 parts by weight of the total aqueous phase.

6. The conductive adhesive composition as in claim 3, wherein hydrophilic monomers and oligomers comprise ethylenically unsaturated, free radically (co)polymerizable, polar species.

7. The conductive adhesive composition as in claim 6, wherein hydrophilic monomers comprise water soluble, ethylenically unsaturated, free radically (co)polymerizable, polar, ionic or nonionic species that are substantially insoluble in the oil phase.

8. The conductive adhesive composition as in claim 7 wherein hydrophilic, water soluble, ethylenically unsaturated, free radically (co)polymerizable, polar, ionic monomers are selected from the group consisting of sodium styrene sulfonate, potassium acrylate, sodium acrylate, sodium methacrylate, ammonium acrylate, sodium 2-acrylamido-2-methylpropane sulfonate, 4,4,9-trimethyl-4-azonia-7-oxa-dec-9-ene-1-sulfonate, N,N-dimethyl-N-(beta-methacryloxyethyl) ammonium propionate betaine, trimethylamine methacrylamide, 1,1-dimethyl-1-(2,3-dihydroxypropyl) amine methacrylamide, and mixtures thereof.

9. The conductive adhesive composition as in claim 6 wherein hydrophilic oligomers are selected from the group consisting of polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures of two or more of the foregoing.

10. The conductive adhesive composition as in claim 9 wherein the hydrophilic oligomers have a number average molecular weight from about 100 to about 100,000.

11. The conductive adhesive composition as in claim 9 wherein the amphiphilic monomers are selected from the group consisting of N-vinylpyrrolidone, N-vinylcaprolactam, (meth)acrylic acid, hydroxyethyl (meth)acrylate, itaconic acid, styrene sulfonic acid, N-substituted acrylamides, N,N-disubstituted acrylamides, N,N-dimethylaminoethyl methacrylate, 2-acrylamido-2-methyl propane sulfonic acid, and mixtures thereof.

12. The conductive adhesive composition as in claim 3 wherein amphiphilic monomers comprise polar ethylenically-unsaturated free-radically (co)polymerizable species partitionable between the aqueous phase and the oil phase of the microemulsion.

13. The conductive adhesive composition as in claim 3 wherein hydrophilic or amphiphilic oligomers comprise polar ethylenically-unsaturated free-radically (co)polymerizable species which are substantially insoluble in the oil phase or which are both water soluble and oil soluble.

14. The conductive adhesive composition as in claim 13 wherein hydrophilic or amphiphilic oligomers are selected from the group consisting of polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures of two or more of the foregoing.

15. The conductive adhesive composition as in claim 3 wherein the polymerizable microemulsion further comprises at least one initiator.

16. The conductive adhesive composition as in claim 3 wherein the hydrophobic monomers comprise free-radically polymerizable, ethylenically-unsaturated species selected from the group consisting of $C_1$ to $C_{18}$ alkyl esters of acrylic acid.

17. The conductive adhesive composition as in claim 16, wherein the hydrophobic monomer comprises one or more alkyl acrylate selected from the group consisting of isooctyl acrylate, 2-ethylhexyl acrylate, n-butyl acrylate and combinations of two or more of the foregoing.

18. The conductive adhesive composition as in claim 3 further comprising lipophilic additive.

19. The conductive adhesive composition as in claim 18 wherein the lipophilic additive comprises a free radically reactive, hydrophobic, crosslinking agent(s) selected from the group consisting of divinylbenzene, 1,4-butanediol diacrylate, 1,6-hexanediol diacrylate, 1,8-octanediol diacrylate; and mixtures of two or more of the foregoing.

20. The conductive adhesive composition as in claim 18 wherein the lipophilic additive comprises a free radically reactive, hydrophobic, chain transfer agent selected from the group consisting of carbon tetrabromide, alcohol, mercaptan, and mixtures of two or more of the foregoing.

21. The conductive adhesive composition as in claim 20 wherein the chain transfer agent is isooctylthioglycolate.

22. The conductive adhesive composition as in claim 3 wherein the surfactant comprises a non-(co)polymerizable surfactant.

23. The conductive adhesive composition as in claim 3 wherein the surfactant comprises a polymerizable surfactant.

24. The conductive adhesive composition as in claim 3 wherein the surfactant is selected from nonionic, anionic and cationic.

25. The conductive adhesive composition of claim 2 wherein the bicontinuous composition is substantially non-porous.

26. The conductive adhesive composition as in claim 1, wherein the organic chloride comprises onium chloride selected from the group consisting of quaternary ammonium chloride, phosphonium chloride, oxonium chloride, sulfonium chloride or mixtures of two or more of the foregoing.

27. The conductive adhesive composition as in claim 26, wherein quaternary ammonium chloride is selected from the group consisting of hydroxyethyl-trimethylammonium chloride, benzyltrimethylammonium chloride, benzyltriethylammonium chloride tetraethylammonium chloride, acetamidopropyl trimethylammonium chloride, lactamidopropyl trimethylammonium chloride, dodecyl trimethylammonium chloride, hexadecyl trimethylammonium chloride, octadecyl trimethylammonium chloride, behenyl trimethylammonium chloride, coconut alkyl trimethylammonium chloride, tetradecyl dimethylbenzylammonium chloride, almondamidopropalkonium chloride, avocadamidopropalkonium chloride, bis-hydroxyethyl tallowmonium chloride, dibehenyldimonium chloride, diocodimonium chloride, didecyldimonium chloride, disoydimonium chloride, ditallowedimonium chloride, ditallowedimonium chloride, PPG-9 diethylmonium chloride, PPG-9 diethylmonium chloride, stearyl ethylhexyldimonium chloride, and combinations of two or more of the foregoing.

28. The conductive adhesive composition of claim 1, wherein the humectant is selected from the group consisting of glycerin, propylene glycol, dipropylene glycol, 1,3-butanediol, 1,4-butanediol, trimethylolpropane, ethylene glycol and combinations of two or more of the foregoing.

29. The conductive adhesive composition of claim 1 wherein the humectant is given by the formula:

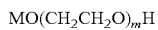

wherein
M is selected from the group consisting of hydrogen and $C_1$ through $C_6$ alkyl; and m is an integer of about 1 to about 25.

30. The conductive adhesive composition of claim 1 wherein the pressure sensitive adhesive is a hydrogel.

31. A biomedical electrode, comprising:
(a) a conductor member; and
(b) a conductive adhesive composition associated with the conductor member, the conductive adhesive composition, comprising:
(i) pressure sensitive adhesive;
(ii) electrolyte comprising water soluble or water dispersible organic chloride; and
(iii) humectant,
wherein the electrolyte and the humectant are at least partially miscible in one another.

32. A biomedical electrode as in claim 31, wherein the conductor member comprises a backing and a conductive component associated with the backing; the conductive adhesive composition comprising first and second major surfaces, the first major surface of the conductive adhesive operatively associated with the conductive component so that electrical current is able to pass through the conductive adhesive to the conductive component or through the conductive component to the conductive adhesive.

33. A biomedical electrode as in claim 32 further comprising a release liner over the second major surface of the conductive adhesive.

34. A biomedical electrode as in claim 33 wherein the release liner comprises a polymeric backing and a fluorochemical release coating over the polymeric backing.

35. A biomedical electrode as in claim 34 wherein the polymeric backing of the release liner comprises polyester.

36. A biomedical electrode as in claim 31 wherein the pressure sensitive adhesive is a bicontinuous composition derived from a polymerizable microemulsion composition, the microemulsion composition comprising:
(a) an aqueous phase comprising one or more hydrophilic monomers or oligomers and/or one or more amphiphilic monomers or oligomers in water, the water-soluble or water-dispersible organic chloride, and humectant;

(b) an oil phase comprising one or more hydrophobic monomers or oligomers.

37. A biomedical electrode as in claim 36 wherein the bicontinuous composition is substantially non-porous.

38. A biomedical electrode as in claim 36, wherein the organic chloride comprises onium chloride selected from the group consisting of quaternary ammonium chloride, phosphonium chloride, oxonium chloride, sulfonium chloride or mixtures of two or more of the foregoing.

39. A biomedical electrode as in claim 38, wherein quaternary ammonium chloride is selected from the group consisting of hydroxyethyl-trimethylammonium chloride, benzyltrimethylammonium chloride, benzyltriethylammonium chloride tetraethylammonium chloride, acetamidopropyl trimethylammonium chloride, lactamidopropyl trimethylammonium chloride, dodecyl trimethylammonium chloride, hexadecyl trimethylammonium chloride, octadecyl trimethylammonium chloride, behenyl trimethylammonium chloride, coconut alkyl trimethylammonium chloride, tetradecyl dimethylbenzylammonium chloride, almondamidopropalkonium chloride, avocadamidopropalkonium chloride, bis-hydroxyethyl tallowmonium chloride, dibehenyldimonium chloride, diocodimonium chloride, didecyldimonium chloride, disoydimonium chloride, ditallowedimonium chloride, ditallowedimonium chloride, PPG-9 diethylmonium chloride, PPG-9 diethylmonium chloride, stearyl ethylhexyldimonium chloride, and combinations of two or more of the foregoing.

40. A biomedical electrode as in claim 36 wherein hydrophilic monomers and oligomers comprise ethylenically unsaturated, free radically (co)polymerizable, polar species.

41. A biomedical electrode as in claim 40, wherein hydrophilic monomers comprise water soluble, ethylenically unsaturated, free radically (co)polymerizable, polar, ionic or nonionic species that are substantially insoluble in the oil phase.

42. A biomedical electrode as in claim 41, wherein hydrophilic, water soluble, ethylenically unsaturated, free radically (co)polymerizable, polar, ionic monomers are selected from the group consisting of sodium styrene sulfonate, potassium acrylate, sodium acrylate, sodium methacrylate, ammonium acrylate, sodium 2-acrylamido-2-methylpropane sulfonate, 4,4,9-trimethyl-4-azonia-7-oxa-dec-9-ene-1-sulfonate, N,N-dimethyl-N-(beta methacryloxyethyl)ammonium propionate betaine, trimethylamine methacrylamide, 1,1-dimethyl-1-(2,3-dihydroxypropyl)amine methacrylamide, and mixtures thereof.

43. A biomedical electrode as in claim 40, wherein hydrophilic oligomers are selected from the group consisting of polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures of two or more of the foregoing.

44. A biomedical electrode as in claim 36, wherein amphiphilic monomers comprise polar ethylenically-unsaturated free-radically (co)polymerizable species partitionable between the aqueous phase and the oil phase of the microemulsion.

45. A biomedical electrode as in claim 44, wherein the amphiphilic monomers are selected from the group consisting of N-vinylpyrrolidone, N-vinylcaprolactam, (meth)acrylic acid, hydroxyethyl (meth)acrylate, itaconic acid, styrene sulfonic acid, N-substituted acrylamides, N,N-disubstituted acrylamides, N,N-dimethylaminoethyl methacrylate, 2-acrylamido-2-methyl propane sulfonic acid, and mixtures thereof.

46. A biomedical electrode as in claim 36 wherein hydrophilic or amphiphilic oligomers comprise polar ethylenically-unsaturated free-radically (co)polymerizable species which are substantially insoluble in the oil phase or which are both water soluble and oil soluble.

47. A biomedical electrode as in claim 46, wherein hydrophilic or amphiphilic oligomers are selected from the group consisting of polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures of two or more of the foregoing.

48. A biomedical electrode as in claim 36, wherein the hydrophobic monomers comprise free-radically polymerizable, ethylenically-unsaturated species selected from the group consisting of $C_1$ to $C_{18}$ alkyl esters of acrylic acid.

49. A biomedical electrode as in claim 48, wherein the hydrophobic monomer comprises one or more alkyl acrylate selected from the group consisting of isooctyl acrylate, 2-ethylhexyl acrylate, n-butyl acrylate and combinations of two or more of the foregoing.

50. A biomedical electrode as in claim 36, wherein the humectant is selected from the group consisting of glycerin, propylene glycol, dipropylene glycol, 1,3-butanediol, 1,4-butanediol, trimethylol propane, ethylene glycol and combinations of two or more of the foregoing.

51. A biomedical electrode as in claim 36, wherein the humectant is given by the formula:

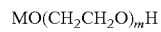

wherein
M is selected from the group consisting of hydrogen and $C_1$ through $C_6$ alkyl; and m is an integer of about 1 to about 25.

52. A biomedical electrode as in claim 36 further comprising lipophilic additive.

53. A biomedical electrode as in claim 52, wherein the lipophilic additive comprises a free radically reactive, hydrophobic, crosslinking agent(s) selected from the group consisting of divinylbenzene, 1,4-butanediol diacrylate, 1,6-hexanediol diacrylate, 1,8-octanediol diacrylate; and mixtures of two or more of the foregoing.

54. A biomedical electrode as in claim 52, wherein the lipophilic additive comprises a free radically reactive, hydrophobic, chain transfer agent selected from the group consisting of carbon tetrabromide, alcohol, mercaptan, and mixtures of two or more of the foregoing.

55. A biomedical electrode as in claim 54, wherein the chain transfer agent is isooctylthioglycolate.

56. A biomedical electrode as in claim 36, wherein surfactant comprises non (co)polymerizable surfactant.

57. A biomedical electrode as in claim 36, wherein the surfactant comprises polymerizable surfactant.

58. A biomedical electrode as in claim 36, wherein the surfactant is selected from nonionic, anionic and cationic surfactants.

59. The conductive adhesive composition of claim 31 wherein the pressure sensitive adhesive is a hydrogel.

* * * * *

UNITED STATES PATENT AND TRADEMARK OFFICE
CERTIFICATE OF CORRECTION

PATENT NO.        : 7,620,439 B2                                              Page 1 of 1
APPLICATION NO. : 11/197216
DATED             : November 17, 2009
INVENTOR(S)       : Vinod P Menon It is certified that error appears in the above-identified patent and that said Letters Patent is hereby corrected as shown below:

Column 1
Line 3, insert heading -- FIELD --.

Column 6
Line 15, Delete "thereof," and insert -- thereof; --, therefor.

Column 7
Line 7, Delete "almond amidopropalkonium" and insert -- almondamidopropalkonium --, therefor.

Column 12
Line 41-42, Delete "polyoxythylene sulfonate, polyoxethylene" and insert
-- polyoxyethylene sulfonate, polyoxyethylene --, therefor.

Column 24
Line 40, Delete "@0%" and insert -- @ 0% --, therefor.

Column 28
Line 12-13, In Claim 27,
after "disoydimonium chloride,"
delete "ditallowedimonium chloride," and insert -- ditallowdimonium chloride, --, therefor.

Line 12-13, In Claim 27, after "ditallowedimonium chloride," delete "ditallowedimonium chloride,".

Column 29
Line 24, In Claim 39,
after "disoydimonium chloride," delete "ditallowedimonium chloride," and insert -- ditallowdimonium
chloride, --, therefor.

Line 25, In Claim 39, before "PPG-9" delete "ditallowedimonium chloride,".

Line 44, In Claim 42,
delete "(beta methacryloxyethyl)" and insert -- (beta-methacryloxyethyl) --, therefor.

Signed and Sealed this

Thirtieth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,620,439 B2  Page 1 of 1
APPLICATION NO. : 11/197216
DATED : November 17, 2009
INVENTOR(S) : Menon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this

Fourteenth Day of December, 2010

David J. Kappos
*Director of the United States Patent and Trademark Office*